United States Patent [19]

Kondo et al.

[11] 4,108,895

[45] Aug. 22, 1978

[54] PROCESS FOR PREPARING CYCLOALKANONE OXIMES

[75] Inventors: Tsuneyuki Kondo, Iwakura; Akio Kuroda, Nagoya, both of Japan

[73] Assignee: Toray Industries, Inc., Tokyo, Japan

[21] Appl. No.: 625,056

[22] Filed: Oct. 23, 1975

[30] Foreign Application Priority Data

Oct. 26, 1974 [JP] Japan .................. 49-123526
Oct. 26, 1974 [JP] Japan .................. 49-123530

[51] Int. Cl.$^2$ .......................... C07C 131/02
[52] U.S. Cl. ............................ 260/566 A
[58] Field of Search ................... 260/566 A

[56] References Cited

PUBLICATIONS

Cotton et al., Advanced Inorganic Chem., 2nd Edition, Interscience Publ., N. Y., p. 355 (1966).
Fitzpatrick et al., J.A.C.S., vol. 78, pp. 530–536 (1956).

*Primary Examiner*—James O. Thomas, Jr.
*Assistant Examiner*—G. T. Breitenstein
*Attorney, Agent, or Firm*—Miller & Prestia

[57] ABSTRACT

A novel process for preparing cycloalkanone oximes is disclosed. The process comprises
(1) contacting a nitrogen compound selected from the group consisting of nitrogen oxides or nitrosyl compounds with an aqueous or an alcoholic solution containing stannous, copper and chlorine ions to prepare hydroxylamine,
(2) allowing a cycloalkanone to react with the hydroxylamine to form an cycloalkanone oxime,
(3) separating the cycloalkanone oxime from the reaction mixture by extraction with an organic solvent at a pH of less than 4.5,
(4) recovering the cycloalkanone oxime from the extract of the step (3),
(5) treating the raffinate of the step (3) under a reducing condition for conversion of stannic ion formed in the step (1) to stannous ion, and
(6) recycling the stannous ion to the step (1)

The process does not produce ammonium salt as a by-product because the cycloalkanone oxime can be separated from the reaction mixture without neutralization.

18 Claims, No Drawings

PROCESS FOR PREPARING CYCLOALKANONE OXIMES

This invention relates to a novel process for preparing a cycloalkanone oxime using nitrogen oxides or nitrosyl compounds as nitrogen source. More specifically this invention relates to a novel process for preparing a cycloalkanone oxime wherein hydroxylamine is prepared by reduction of nitrogen oxides or nitrosyl compounds with stannous ion, and allowed to react with a cycloalkanone to form an oxime, and the cycloalkanone oxime is extracted at pH of less than 4.5 without producing a by-product of ammonium salt.

Cycloalkanone oximes are a raw material for production of polyamides, and have been produced in a large scale by reaction of cycloalkanone with hydroxylamine. In this reaction, however, hydroxylamine is usually fed to the reaction mixture in a form of salt with an inorganic acid. Therefore the reaction mixture should be neutralized with alkali such as ammonium hydroxide, before separating cycloalkanone oxime therefrom. Because of the neutralization step, the by-production of an inorganic salt, usually an ammonium salt, is inevitable on producing cycloalkanone oxime.

For this reason it has been desired to develop a process for producing cycloalkanone oxime which does not produce an ammonium salt as by-product.

We now have found that hydroxylamine prepared by reduction of nitrogen oxides or nitrosyl compounds by stannous ion in an aqueous or an alcoholic solution can be utilized for producing cycloalkanone oximes, which can be isolated from the reaction mixture without neutralization. The reduction of nitric oxide to hydroxylamine by aqueous stannous chloride is disclosed in Inorganic Chemistry, vol. 9, 1912 (1970). But nothing is described about utilization of the hydroxylamine thus obtained.

The present invention is a novel process for production of cycloalkanone oximes which comprises
(1) contacting a nitrogen compound selected from the group consisting of nitrogen oxides or nitrosyl compounds with an aqueous or an alcoholic solution containing stannous, copper and chlorine ions to prepare hydroxylamine,
(2) allowing a cycloalkanone to react with the hydroxylamine to form a cycloalkanone oxime,
(3) separating the cycloalkanone oxime from the reaction mixture by extraction with an organic solvent at a pH of less than 4.5,
(4) recovering the cycloalkanone oxime from the extract of the step (3),
(5) treating the raffinate under a reducing condition for conversion of stannic ion formed in the step (1) to stannous ion, and
(6) recycling the stannous ion to the step (1).

In the first step a nitrogen compound selected from the group consisting of nitrogen oxides or nitrosyl compounds is subjected to contact with an aqueous or an alcoholic solution containing stannous, copper, and chlorine ions. Nitrogen oxides or nitrosyl compounds may be prepared by a conventional method and may be either a substantially pure gas or diluted by an inert gas such as nitrogen or helium.

Among nitrogen oxides, nitric oxide is most preferable. Nitrosyl compounds may be represented by the formula NOX wherein X is fluorine, chlorine, bromine and —$SO_4H$.

As a source of stannous ion, stannous halide such as bromide and chloride, and stannous sulfate may be used. The most preferable stannous source is stannous chloride.

The copper ion may be either cuprous or cupric ion and as a source of those ions, chlorides, bromides, fluorides, sulfate, nitrate and acetates may be used. More than two of these compounds may also be used together. The amount of cupric ion may preferably be less than equivalent to stannous ion, and more preferably 0.5 to 10 mol% on the basis of stannous ion. Cuprous ion may be effectively used in an amount of more than 0.01 mol% on the basis of stannous ion, but more than equivalent amount of cuprous ion does not improve the hydroxylamine yield.

From the economical point of view the preferable amount of cuprous ion may be 0.5 to 30 mol% on the basis of stannous ion.

As the chlorine ion source, hydrogen, ammonium, potassium, sodium and lithium chlorides may be used. Chlorine contained in the sources of stannous and copper ions can also play a role of the chlorine ion source.

The reduction should be carried out in a medium of a protic solvent such as water and alcohols. As an alcohol, cyclohexanol and aliphatic primary alcohol such as methyl, ethyl, propyl, butyl, iso-butyl, amyl alcohols may be preferably used. An aqueous alcohol may also be used. Aqueous medium may be most preferable in the step (1) especially in view of following extraction step to separate the cycloalkanone oxime.

The reaction medium may be prepared by adding and dissolving the sources of stannous, copper and chlorine ions in water or alcohols. The concentration of stanous ions may preferably be more than about 10 wt% calculated as stannous chloride.

The reduction may be carried out in a conventional manner of a gas-liquid reaction. An aqueous or an alcoholic reaction medium may be shaken under the atmosphere of nitrogen oxides or nitrosyl compounds, or those gases may be directly bubbled in the reaction medium.

The reaction may be carried out at a temperature of 0° to 100° C, preferably 0° to 50° C, under atmospheric or superatmospheric pressure.

In the reduction step (1) the addition of phophoric acid or its salts and/or boric acid or its salts may enhance the yield of hydroxylamine.

As phosphoric salt, potassium dihydrogenphosphate, sodium dihydrogenphosphate, ammonium dihydrogenphosphate, sodium ammonium hydrogenphosphate, dipotassium hydrogenphosphate, diammonium hydrogenphosphate, ammonium phosphate, may preferably be used. As boric salt, sodium borate, potassium borate, and ammonium borate, may preferably be used. The amount of those additives is not restricted, but the preferable amount is 0.01 to 1 mol per stannous ion. Sulfuric acid may also be added to the reaction medium of the step (1) for the same purpose.

Hydoxylamine, formed in the reduction step (1), is subjected to react with a cycloalkanone to form a cycloalkanone oxime in the step (2).

The cycloalkanone may have a 5 to 12 carbon atoms. The prosess of the present invention may be most suitable for production of cyclohexanoneoxime, but other oximes such as cyclododecanoneoxime can advantageously be produced by the process.

The cycloalkanone may previously be added to the reaction medium of the reduction step (1). In this case hydroxylamine may react with the cycloalkanone just after it is formed. The cycloalkanone may also be added to the reaction mixture containing hydroxylamine after the feed of nitrogen oxides or nitrosyl compounds are terminated.

The cycloalkanone may optionally be fed to the reaction mixture in a continuous manner concurrently with the feed of nitrogen oxides or nitrosyl compounds. When the reduction step (1) is carried out in an aqueous medium, the cycloalkanone may be added to the reaction medium in a form of solution in an organic solvent immiscible with water. The solution may form organic phase in the reaction medium, and the cycloalkanone is continuously fed therefrom to the aqueous phase, in which the reduction takes place.

The amount of cycloalkanone may be at least equivalent to the hydroxlamine but preferably 0.1 to 1.0 molar excess of cycloalkanone is added to the reaction mixture, because the following extraction step (3) may require such an excess of cycloalkanone as mentioned below.

The oximation reaction may be carried out at room temperature. Preferable reaction temperature may be 0° to 50° C.

The cycloalkanone oxime thus prepared is separated from the reaction mixtures by extraction. In the process of the present invention the extraction is carried out at a pH of less than 4.5.

An oxime is generally hydrolized to a corresponding carbonyl compound and hydroxylamine in an acidic solution. The degree of the hydration depends on the acidity of the solution. Therefore on extracting an oxime from acidic solution, the solution is generally neutralized to a pH of more than 4.5 by adding an alkali such as ammonium hydroxide. In the process of the present invention, however, the cycloalkanone oxime can be extracted from the reaction mixture at a pH of less than 4.5, if an excess of cycloalkanone is present in the reaction mixture. Cycloalkanone may preferably be at least 1.1 mol per mol of hydroxylamine.

When the reduction step (1) is carried out in an alcoholic medium, the reaction mixture may be mixed with water, and then be extracted with an organic solvent. The alcohol may be removed from the mixture together with cycloalkanone oxime. The raffinate may be an aqueous solution containing stannic ion, and may be transferred to the following reduction step (5).

The extraction solvent may preferably be an oxygen containing organic solvent such as aliphatic or alicyclic ethers and carboxylic esters having a carbon number of 4 to 12. Diethyl ether, diisopropyl ether, dicyclohexyl ether, butyl acetate, isobutyl acetate, isopropyl acetate, n-propyl acetate, cyclohexyl acetate may be used as the extraction solvent. In the step (3), the extraction can be operated in a conventional manner either continuously or batchwisely. The operating temperature may be room temperature or an elevated temperature up to the boiling point of the solvent. From the economical point of view the extraction may preferably be operated at room temperature.

From the extract of the extraction step (3) the cycloalkanone oxime may be recovered by a conventional method such as distillation. The raffinate of the extraction step (3) contains stannic ion produced by oxidation of stannous ion in the reduction step (1). The stannic ion is reduced to stannous ion according to a conventional method such as catalytic, stoichiometric or electrochemical reduction in the step (5). The reduction of stannic ion may preferably be subjected to the catalytic hydrogenation using noble metal catalyst. Platinum on an inert carrier may preferably used as a catalyst. Platinum on carbon is most preferable. The catalytic hydrogenation may be carried out under atmospheric or superatmospheric pressure at a temperature of 0° to 100° C. The amount of platinum metal used as the catalyst is 0.01 to 10 mol% on the basis of stannic ion.

Generally the existence of a copper ion in the raffinate does not give a good effect to the catalytic hydrogenation of stannic ion. We, however, have found that cupric chloride, cuprous and cupric bromide, cupric fluoride and curpic hydroxide do not disturb the hydrogenation. Hydrogen chloride or ammonium chloride may preferably added to the raffinate before the reduction of step (5), and thereby the yield of stannous ion is improved.

When the raffinate of the extraction step is transferred to the reducing step (5), the raffinate may be preferably treated, for instance with active carbon, to remove by-products in the previous steps and contaminants that disturb the following reduction of stannic ion.

The stannous ion containing solution thus obtained is recycled to the reduction step (1), and can repeatedly be utilized to reduce nitrogen oxides and nitrosyl compounds to hydroxylamine.

According to the process of the present invention cycloalkanone oximes can be produced at a high yield from nitrogen oxides or nitrosyl compounds. The process also have a merit in the energy consumption because all the steps can be operated at a comparatively low temperature. Furthermore the process is quite advantageous because it does not produce by-product of an inorganic salt such as ammonium sulfate originated from neutralization.

The following examples shall further exemplify the present invention, but not restrict the same.

In the examples the cycloalkanone oxime yield is calculated on the basis of theoretical amounts of cycloalkanone oxime produced from the initially charged stannous ion according to the following equation.

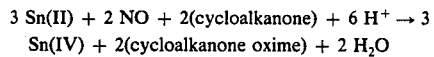

$$3\ Sn(II) + 2\ NO + 2(cycloalkanone) + 6\ H^+ \rightarrow 3\ Sn(IV) + 2(cycloalkanone\ oxime) + 2\ H_2O$$

EXAMPLE 1

Stannous chloride dihydrate ($SnCl_2 \cdot 2H_2O$, 5 mmol) and cuprous chloride (CuCl, 0.3 mmol) are placed with 5 ml of water in a glass tube (about 20 mm diameter and 150 mm height) equipped with a stop cock at the side arm of the tube.

This tube is set to a vibrating apparatus and is shaken vigorously in nitric oxide (NO) gas atmosphere at room temperature. The amount of NO gas absorbed in the solution is followed at regular intervals by weight increase.

After four hours of vibration, by this time the solution is almost saturated with NO gas and no more absorption is detected, the NO gas is replaced by nitrogen gas and 3.4 mmol of cyclohexanone is added to the solution.

The acidic mixture is then neutralized with ammonium hydroxide ($NH_4OH$).

The cyclohexanoneoxime formed in the mixture is extracted with chloroform and subjected to analysis by gaschromatography.

The yield of cyclohexanoneoxime is 83.4 mol% based on $SnCl_2 \cdot 2H_2O$.

EXAMPLE 2

The procedure of Example 1 is repeated using $SnCl_2.2H_2O$ with various copper compounds as promoters under different conditions. The results are given in Table I.

Table I

| Exp. No. | $SnCl_2 . 2H_2O$ mmol | Cu Comps. added Formula | mmol | Temp °C | Time hr | Cyclohexanone-oxime Yield mol% |
|---|---|---|---|---|---|---|
| 2- 1 | 5 | $CuSO_4$ | 0.3 | 25 | 4.0 | 80.3 |
| 2- 2 | " | CuBr | " | " | " | 84.9 |
| 2- 3 | " | $CuBr_2$ | " | " | " | 76.2 |
| 2- 4 | " | $CuF_2$ | " | " | " | 80.6 |
| 2- 5 | " | $Cu(NO_3)_2$ | " | " | " | 82.1 |
| 2- 6 | " | $Cu(CH_3COO)_2$ | " | " | " | 78.2 |
| 2- 7 | " | $CuCl_2$ | " | " | " | 80.6 |
| 2- 8 | " | " | 0.5 | " | " | 80.9 |
| 2- 9 | " | " | 0.01 | " | " | 57.1 |
| 2-10 | " | " | 2.0 | " | " | 72.9 |
| 2-11 | " | " | 5.0 | " | " | 10.9 |
| 2-12 | " | " | 10.0 | " | " | Trace |
| 2-13 | " | CuCl | 0.01 | " | " | 62.1 |
| 2-14 | " | " | 2.0 | " | " | 81.0 |
| 2-15 | " | " | 5.0 | " | " | 82.4 |
| 2-16 | " | " | 10.0 | " | " | 82.0 |
| 2-17 | " | " | 0.3 | " | 0.5 | 31.9 |
| 2-18 | " | " | " | " | 1.0 | 53.6 |
| 2-19 | " | " | " | " | 2.0 | 77.6 |
| 2-20 | " | " | " | " | 6.0 | 81.8 |
| 2-21 | " | " | " | 5 | 4.0 | 79.8 |
| 2-22 | " | " | " | 40 | " | 80.3 |
| 2-23 | " | " | " | 50 | " | 81.6 |
| 2-24 | " | " | " | 60 | " | 81.2 |
| 2-25 | 10 | " | 0.6 | 25 | " | 85.6 |

EXAMPLE 3

The procedure of Example 1 is repeated except that water is replaced by 5 ml of hydrochloric acid (HCl) aqueous solution with different concentration. The results are shown in Table II.

Table II

| Exp. No. | HCl mmol/5ml-soln. | Cyclohexanoneoxime Yield mol% |
|---|---|---|
| 3-1 | 1 | 87.2 |
| 3-2 | 2 | 85.0 |
| 3-3 | 3 | 84.1 |
| 3-4 | 4 | 83.2 |
| 3-5 | 6 | 82.5 |

EXAMPLE 4

The procedure of Example 2 is repeated except that cyclohexanone is added to the solution before NO gas absorption. The results are given in Table III.

Table III

| Exp. No. | $SnCl_2 . 2H_2O$ mmol | Cu Comps. Formula | mmol | HCl mmol/5ml-soln. | Temp. °C | Time hr | Cyclohexanone-oxime Yield mol% |
|---|---|---|---|---|---|---|---|
| 4- 1 | 5 | $CuSO_4$ | 0.3 | 0 | 25 | 4.0 | 79.7 |
| 4- 2 | " | CuBr | " | " | " | " | 84.5 |
| 4- 3 | " | $CuBr_2$ | " | " | " | " | 73.8 |
| 4- 4 | " | $CuF_2$ | " | " | " | " | 79.9 |
| 4- 5 | " | $Cu(NO_3)_2$ | " | " | " | " | 81.2 |
| 4- 6 | " | $Cu(CH_3COO)_2$ | " | " | " | " | 76.9 |
| 4- 7 | " | $CuCl_2$ | " | " | " | " | 79.8 |
| 4- 8 | " | " | 0.5 | " | " | " | 80.1 |
| 4- 9 | " | " | 0.01 | " | " | " | 56.8 |
| 4-10 | " | " | 2.0 | " | " | " | 71.6 |
| 4-11 | " | " | 5.0 | " | " | " | 10.7 |
| 4-12 | " | " | 10.0 | " | " | " | Trace |
| 4-13 | " | CuCl | 0.01 | " | " | " | 59.7 |
| 4-14 | " | " | 2.0 | " | " | " | 80.8 |
| 4-15 | " | " | 10.0 | " | " | " | 81.0 |
| 4-16 | " | " | 0.3 | " | " | 0.5 | 30.9 |
| 4-17 | " | " | " | " | " | 1.0 | 52.3 |
| 4-18 | " | " | " | " | " | 2.0 | 75.0 |
| 4-19 | " | " | " | " | " | 6.0 | 80.5 |
| 4-20 | " | " | " | " | 5 | 4.0 | 78.6 |
| 4-21 | " | " | " | " | 40 | " | 79.3 |
| 4-22 | " | " | " | " | 50 | " | 78.2 |
| 4-23 | " | " | " | " | 60 | " | 57.3 |
| 4-24 | " | " | " | 1.0 | 25 | " | 86.9 |
| 4-25 | " | " | " | 2.0 | " | " | 84.2 |
| 4-26 | " | " | " | 3.0 | " | " | 83.2 |
| 4-27 | " | " | " | 4.0 | " | " | 82.7 |
| 4-28 | " | " | " | 6.0 | " | " | 81.9 |
| 4-29 | 10.0 | " | 0.6 | 0 | " | " | 84.8 |

EXAMPLE 5

The procedure of Example 1 is repeated except that cyclohexanone is added with 5 ml of organic solvent before NO gas absorption. The results are given in Table IV.

Table IV

| Exp. No. | Organic Solvent 5 ml | Cyclohexanoneoxime Yield mol% |
|---|---|---|
| 5-1 | Chloroform | 81.2 |
| 5-2 | Benzene | 82.0 |
| 5-3 | Cyclohexane | 81.6 |
| 5-4 | Hexane | 80.9 |

EXAMPLE 6

The procedure of Example 1 is repeated except that water is replaced by one of the primary alcohols cited in Table V. The results are shown in the table.

Table V

| Exp. No. | Primary Alcohols 5 ml | Cu Comps. 0.3mmol | Cyclohexanoneoxime Yield mol% |
|---|---|---|---|
| 6-1 | Methyl Alcohol | CuCl | 30.6 |
| 6-2 | Ethyl Alcohol | " | 37.4 |
| 6-3 | n-Propyl Alcohol | " | 35.8 |
| 6-4 | n-Butyl Alcohol | " | 50.3 |
| 6-5 | i-Butyl Alcohol | " | 29.5 |
| 6-6 | n-Amyl Alcohol | " | 45.6 |
| 6-7 | Methyl Alcohol | $CuCl_2$ | 28.6 |
| 6-8 | " | CuBr | 31.7 |
| 6-9 | " | $CuBr_2$ | 28.2 |
| 6-10 | " | $CuF_2$ | 29.3 |
| 6-11 | " | $Cu(NO_3)_2$ | 29.6 |
| 6-12 | " | $Cu(CH_3COO)_2$ | 30.1 |

EXAMPLE 7

The procedure of Example 1, 2 or 6 is repeated except that NO gas is replaced by one of the nitrosyl compounds cited in Table VI. The results are shown in the table.

Table VI

| Exp. No. | Water or Alcohols 5 ml | Cu Comps 0.3mmol | Nitrosyl Comps | Cyclohexanone-oxime Yield mol% |
|---|---|---|---|---|
| 7-1 | $H_2O$ | CuCl | NOCl | 56.2 |
| 7-2 | " | $CuCl_2$ | " | 48.7 |
| 7-3 | " | CuBr | " | 55.0 |
| 7-4 | " | $CuBr_2$ | " | 51.3 |
| 7-5 | " | $CuSO_4$ | " | 58.2 |
| 7-6 | " | $Cu(NO_3)_2$ | " | 55.5 |
| 7-7 | " | $Cu(CH_3COO)_2$ | " | 53.0 |
| 7-8 | Methyl Alcohol | CuCl | " | 29.1 |
| 7-9 | Ethyl Alcohol | " | " | 32.8 |
| 7-10 | Propyl Alcohol | " | " | 36.4 |
| 7-11 | n-BUtyl Alcohol | " | " | 39.7 |
| 7-12 | i-Butyl Alcohol | " | ' | 21.9 |
| 7-13 | n-Amyl Alcohol | " | " | 43.5 |
| 7-14 | $H_2O$ | " | NOBr | 35.3 |
| 7-15 | " | " | $NOHSO_4$ | 21.1 |

EXAMPLE 8

The procedure of Example 1, 5 or 7 is repeated except that cyclohexanol is used instead of water. The results are shown in Table VII.

Table VII

| Exp. No. | Cyclo-hexanol ml | Organic Solvent name | ml | NO or NOCl | Cyclohexanone-oxime Yield mol% |
|---|---|---|---|---|---|
| 8-1 | 5.0 | — | — | NO | 9.7 |
| 8-2 | 1.0 | Benzene | 4 | " | 2.1 |
| 8-3 | 1.0 | Cyclohexanone | 4 | " | 34.1 |
| 8-4 | 5.0 | — | — | NOCl | 7.6 |

EXAMPLE 9

The procedure of Example 1 is repeated except that cyclododecanone is used instead of cyclohexanone. Production of cyclododecanoneoxime is confirmed by gaschromatography.

EXAMPLE 10

The procedure of Exp. No. 2-1 in Example 2 is repeated except that stannous sulfate ($SnSO_4$) or stannous bromide ($SnBr_2$) is used instead of $SnCl_2.2H_2O$. The results under various conditions are given in Table VIII.

Table VIII

| Exp. No. | Stannous Comps. Formula | mmol | Cu Comps. Formula | mmol | Cl Comps. or Salt Formula | mmol | Solv. 5 ml | Cyclo-hexanone-oxime Yield mol% |
|---|---|---|---|---|---|---|---|---|
| 10-1 | $SnSO_4$ | 5 | $CuSO_4$ | 0.5 | $NH_4Cl$ | 10 | $N-H_2SO_4$ | 62.5 |
| 10-2 | " | " | " | " | " | " | $H_2O$ | 49.8 |
| 10-3 | " | " | " | " | NaCL | " | " | 43.8 |
| 10-4 | " | " | " | " | KCl | " | " | 60.5 |
| 10-5 | " | " | — | — | HCl | 5 | " | 50.1 |
| 10-6 | " | " | CuCl | 0.5 | $NH_4Cl$ | 10 | $N-H_2SO_4$ | 58.2 |
| 10-7 | $SnBr_2$ | " | CuBr | " | " | " | " | 25.7 |
| 10-8 | " | " | " | " | " | " | $H_2O$ | 17.6 |

EXAMPLE 11

The procedure of Example 1 is repeacted except that the chloroform is replaced by one of the organic solvents shown in Table IX, and the amount of cyclohexanone is about 1.5 times in excess of the hydroxylamine produced, and that cyclohexanoneoxime is extracted without neutralization.

The extraction efficiency of cyclohexanoneoxime (%OX) is calculated by the following equation.

$$\% \, OX = \frac{\text{[moles of the extracted cyclohexanoneoxime]}}{\text{[moles of the produced cyclohexanoneoxime in the reaction mixture]}} \times 100$$

The results are given in the table.

Table IX

| Exp. No. | Organic Solvent | % OX mol% | Separation |
|---|---|---|---|
| 11-1 | Diethyl Ether | 73.2 | Good |
| 11-2 | Diisopropyl Ether | 66.9 | " |
| 11-3 | n-Butyl Acetate | 53.5 | " |
| 11-4 | i-Butyl Acetate | 43.0 | " |
| 11-5 | n-Propyl Acetate | 55.8 | " |
| 11-6 | i-Propyl Acetate | 63.5 | " |
| 11-7 | Chloroform | 38.9 | " |
| 11-8 | Toluene | 21.8 | Bad |
| 11-9 | Benzene | 29.8 | " |
| 11-10 | Ethyl Benzene | — | Inseparable |
| 11-11 | Xylene | 8.9 | Bad |
| 11-12 | Petroleum Ether | 7.0 | " |
| 11-13 | Metyl Cyclohexane | 4.0 | " |

Table IX-continued

| Exp. No. | Organic Solvent | % OX mol% | Separation |
|---|---|---|---|
| 11-14 | n-Heptane | 3.0 | " |
| 11-15 | Cyclohexane | — | Inseparable |
| 11-16 | Petroleum Benzine | — | " |
| 11-17 | Chlorobenzene | — | " |

These results show that cyclohexanoneoxime is effectively extracted using the suitable solvents as shown in the Exp. No. 1~6, even in strong acidic condition (pH 1~2) without neutralization.

EXAMPLE 12

Cyclohexanone (0.25 ml) is added to the raffinate of Exp. No. 11-1 of Example 11, and the cyclohexanoneoxime is extracted with 50 ml of diethyl ether. This operation is repeated once again. The overall %OX is 90.1 mol%.

The same operation is further repeated seven times in succession. In total, 99.4 mol% of extraction efficency is obtained.

EXAMPLE 13

Stannous chloride dihydrate (0.1 mol) and cuprous chloride (0.015 mol) are placed in a glass reactor (45 mm diameter and 90 mm height) equipped with a gas inlet tube at the center and an outlet on the shoulder, and 100 ml of water is added. NO gas is bubbled through a porous sintered glass ball-filter, into the solution. The NO gas is supplied froma gas reservoir and the unreacted NO gas is recycled to it by means of a gas circulating pump.

The amount of NO gas absorbed in the solution is measured at regular intervals by a gas buret attached to the reservoir.

When NO gas is saturated in the solution and no more absorption is detected, NO gas is purged out and replaced by nitrogen gas, and then 0.34 mol of cyclohexanone is added to the solution. The mixture is neutralized with ammonium hydroxide aqueous solution. Hydroxylamine is liberated and reacts with cyclohexanone to produce cyclohexanoneoxime which is then extracted each with 300 ml of chloroform for three times.

The chloroform is evaporated and the residue is subjected to gaschromatography analysis. The yield of 93.5 mol% is obtained.

EXAMPLE 14

The procedure of Example 13 is repeated except that one of the salts shown in Table X is added as an additional promoter. The results are summarized in the table.

Table X

| Exp. No. | Salts added Formula | mmol | Cyclohexanoneoxime Yield mol% |
|---|---|---|---|
| 14- 1 | $KH_2PO_4$ | 18 | 96.5 |
| 14- 2 | " | 37 | 99.9 |
| 14- 3 | " | 55 | 99.7 |
| 14- 4 | $NaH_2PO_4$ | 36 | 97.1 |
| 14- 5 | $NH_4H_2PO_4$ | 43 | 95.3 |
| 14- 6 | $NaNH_4HPO_4$ | 24 | 94.8 |
| 14- 7 | $K_2HPO_4$ | 29 | 94.2 |
| 14- 8 | $(NH_4)_2HPO_4$ | 38 | 94.1 |
| 14- 9 | $(NH_4)_3PO_4$ | 25 | 93.8 |
| 14-10 | $Na_2B_4O_7$ | 46 | 94.2 |
| 14-11 | $K_2B_4O_7$ | 62 | 93.9 |
| 14-12 | $(NH_4)_2B_4O_7$ | 65 | 94.0 |
| 14-13 | $H_3PO_4$ | 43 | 93.7 |
| 14-14 | $CH_3COONa$ | 12 | 80.7 |
| 14-15 | $CH_3COONH_4$ | 20 | 86.0 |
| 14-16 | NaCl | 72 | 87.9 |

Table X-continued

| Exp. No. | Salts added Formula | mmol | Cyclohexanoneoxime Yield mol% |
|---|---|---|---|
| 14-17 | KCl | 67 | 86.7 |
| 14-18 | $NH_4Cl$ | 73 | 87.1 |

These results show unexpected high yield of cyclohexanoneoxime is obtained by the addition of such salts as shown in Exp. No. 1~13, especially in No. 1~3.

EXAMPLE 15

To a 25 ml of aqueous solution containing stannic chloride pentahydrate ($SnCl_4.5H_2O$, 20 mmol), cupric chloride ($CuCl_2$, 3 mmol), and HCl (20 mmol), is added 1.5 grams of 10% platinum on carbon catalyst. Hydrogen is introduced at atmospheric pressure and Sn(IV) is catalytically reduced to Sn(II). The temperature is maintained at about 25° C throughout the reaction.

At the end of eight hours, the mixture is filtered through a glass filter to remove any particles of carbon supported catalyst. The precipitate is washed with small amount of water.

NO gas is bubbled into the filtrate using the same apparatus and procedure as described in Example 13.

The yield of cyclohexanoneoxime based on initially charged $SnCl_4.5H_2O$ is 64.1 mol%.

EXAMPLE 16

The procedure of Example 15 is repeated except that cupric chloride is replaced by one of the copper compounds shown in Table XI and the amounts of it is changed as indicated. The resuls are also shown in the table.

Table XI

| Exp. No. | Copper Comps added Formula | mmol | Cyclohexanoneoxime Yield mol% |
|---|---|---|---|
| 16-1 | $CuBr_2$ | 1.0 | 73.2 |
| 16-2 | " | 3.0 | 78.4 |
| 16-3 | " | 4.2 | 76.4 |
| 16-4 | $CuCl_2$ | 1.0 | 66.9 |
| 16-5 | " | 3.8 | 63.8 |
| 16-6 | CuBr | 3.0 | 64.5 |
| 16-7 | $CuF_2$ | 3.0 | 61.3 |
| 16-8 | $Cu(OH)_2$ | 1.0 | 70.3 |
| 16-9 | " | 4.1 | 67.6 |

EXAMPLE 17

The procedure of Example 15 is repeated except that ammonium chloride ($NH_4Cl$, 80 mmol) is added to the mixture as a promoter. The yield of cyclohexanoneoxime is 76.3 mol%.

EXAMPLE 18

The procedure of Example 15 or 17 is repeated except that HCl is omitted. The yields of cyclohexanoneoxime are 57.2 mol% and 69.7 mol% respectively.

EXAMPLE 19

The procedure of Example 15, 17 or 18 is repeated except that the catalytic reduction of Sn(IV) is performed under superatmospheric hydrogen pressure using an autoclave. The results are summarized in Table XII.

Table XII

| Exp. No. | HCl added mmol | NH₄Cl added mmol | Pressure of Hydrogen kg/cm² | Cyclohexanone-oxime Yield mol% |
|---|---|---|---|---|
| 19- 1 | 20 | — | 5 | 80.1 |
| 19- 2 | " | — | 10 | 81.6 |
| 19- 3 | " | — | 20 | 82.9 |
| 19- 4 | " | — | 40 | 83.2 |
| 19- 5 | " | 80 | 5 | 89.4 |
| 19- 6 | " | " | 10 | 92.3 |
| 19- 7 | — | — | 5 | 68.7 |
| 19- 8 | — | — | 10 | 70.2 |
| 19- 9 | — | 80 | 5 | 76.2 |
| 19-10 | — | " | 10 | 78.5 |

EXAMPLE 20

Stannic chloride pentahydrate ($SnCl_4 \cdot 5H_2O$, 20 mmol), cupric chloride ($CuCl_2$, 3 mmol), and hydrochloric acid (HCl, 20 mmol) are charged with 25 ml of water in the same reactor as described in Example 15. Then 1.5 grams of 10% platinum on carbon catalyst are suspended in the solution, and hydrogen gas is bubbled into the mixture, Sn(IV) is reduced to Sn(II) at room temperature under atmospheric pressure. The reaction is continued for eight hours and then the catalyst is separated by filtration.

The filtrate is transferred into another reactor and NO gas is bubbled into it until it is saturated, followed by the oximation reaction by the addition of about 0.51 mol of cyclohexanone as described in Example 11.

Cyclohexanoneoxime is extracted from the reaction mixture with diethyl ether for ten times in succession without neutralization.

Small amounts of diethyl ether dissolved in the raffinate (aqueous solution) is removed by evaporation, and the aqueous solution is then purified with active carbon to remove any trace of contaminants. The concentration of $CuCl_2$ in the purified aqueous solution is adjusted to 3 mmol and the solution is again transferred into another reactor.

To the solution, is added 1.5 grams of 10% platinum on carbon catalyst, and the same procedures as described above are repeated.

The yield of cyclohexanoneoxime in the first run is 64.8 mol% and that of the second run is 55.8 mol% which lead to the total yield of 120.6 mol% based on initially charged $SnCl_4 \cdot 5H_2O$.

What we claim is:

1. A continuous process for preparing a cycloalkanone oxime which comprises:
   (1) contacting a nitrogen compound selected from the group consisting of nitrogen oxides and nitrosyl compounds with an aqueous or an alcoholic solution containing stannous ion, copper ion and chlorine ion wherein the amount of copper is more than 0.01 mole % on the basis of stannous ion, at a temperature of 0 to 100° C under atmospheric or superatmospheric pressure to prepare hydroxylamine,
   (2) causing the hydroxylamine to react with an excess amount of a cycloalkanone having 5 to 12 carbon atoms at a temperature of 0 to 50° C to form a cycloalkanone oxime,
   (3) separating the cycloalkanone oxime from the reaction mixture by extraction with an organic solvent selected from the group consisting of aliphatic or alicyclic ethers and carboxylic esters having a carbon number of 4 to 12 at a pH of less than 4.5,
   (4) recovering the cycloalkanone oxime from the extract of the step (3),
   (5) treating the raffinate of the step (3) under atmospheric or superatmospheric pressure at a temperature of 0° to 100° C under a reducing condition for conversion of stannic ion formed in the step (1) to stannous ion, and
   (6) recycling the stannous ion to the step (1).

2. A process of claim 1 wherein the nitrogen compound is nitric oxide.

3. A process of claim 1 wherein the nitrogen compound is a nitrosyl compound represented by the formula NOX wherein X is fluorine chlorine, bromine, and —SO₄H.

4. A process of claim 1 wherein the stannous ion is added to the reaction medium of the step (1) in a form of stannous salt selected from the group consisting of stannous chloride, bromide and sulfate.

5. A process of claim 4 wherein the stannous salt is stannous chloride.

6. A process of claim 1 wherein the copper ion is added to the reaction medium of the step (1) in a form of cuprous or cupric salt selected from the group consisting of copper chlorides, bromides, fluorides, sulfate, nitrate and acetates.

7. A process of claim 6 wherein the copper ion is added to the reaction medium of the step (1) in a form of cuprous chloride.

8. A process of claim 6 wherein the copper ion is added to the reaction medium of the step (1) in a form of cupric chloride.

9. A process of claim 1 wherein the chlorine ion is added to the reaction mixture in a form of inorganic chloride selected from the group consisting of hydrochloric acid, stannous, stannic, ammonium, potassium, sodium and lithium chlorides.

10. A process of claim 1 wherein the step (1) is carried out in an aqueous medium.

11. A process of claim 1 wherein the step (1) is carried out in an alcoholic medium using cyclohexanal and an aliphatic primary alcohol selected from the group consisting of methyl, ethyl, propyl, butyl, iso-butyl, and amyl alcohols.

12. A process of claim 1 wherein the cycloalkanone is cyclohexanone.

13. A process of claim 1 wherein the reduction of stannic ion to stannous ion is carried out by catalytic hydrogenation using a noble metal catalyst.

14. A process of claim 13 wherein the noble metal catalyst is platinum on carbon.

15. A process of claim 13 wherein the catalytic hydrogenation is carried out in the presence of hydrochloric acid or ammonium chloride.

16. A process of claim 1 wherein the reaction medium of the step (1) further contains an acid selected from the group consisting of sulfuric, phosphoric and boric acids.

17. A process of claim 1 wherein the reaction medium of the step (1) further contains a phosphoric or boric acid salt selected from the group consisting of potassium dihydrogenphoophate, sodium dihydrogenphosphate, ammonium dihydrogenphosphate, sodium ammonium hydrogenphosphate, dipotasoium hydrogenphosphate, diammonium hydrogenphosphate, ammonium phosphate, sodium borate, potassium borate and ammonium borate.

18. A process for preparing a cycloalkanone oxime which comprises:
   (1) contacting a nitrogen compound selected from the group consisting of nitrogen oxide and a nitrosyl compound of the formula NOX, wherein X is selected from the group consisting of chlorine, bromine and —SO$_4$H, with an aqueous or alcoholic solution containing stannous ion, copper ion and chlorine ion, wherein the amount of copper ion is more than 0.01 mol % on the basis of stannous ion, at a temperature of 0° to 100° C under atmospheric or superatmospheric pressure to prepare hydroxylamine, (2) causing the hydroxylamine to react with an excess amount of cycloalkanone having 5 to 12 carbon atoms at a temperature of 0° to 50° C to form a cycloalkanone oxime, (3) separating the cycloalkanone oxime from the reaction mixture by extraction with an organic solvent selected from the group consisting of aliphatic or alicyclic ethers and carboxylic esters having a carbon number of 4 to 12 at a pH of less than 4.5, and (4) recovering the cycloalkanone oxime from the extract.

* * * * *